United States Patent [19]
Holmström

[11] Patent Number: 5,391,191
[45] Date of Patent: Feb. 21, 1995

[54] DEVICE FOR TISSUE STIMULATION
[75] Inventor: Nils Holmström, Järfälla, Sweden
[73] Assignee: Siemens Aktiengesellschaft, Munich, Germany
[21] Appl. No.: 924,025
[22] PCT Filed: Apr. 23, 1991
[86] PCT No.: PCT/EP91/00779
§ 371 Date: Aug. 26, 1992
§ 102(e) Date: Aug. 26, 1992
[87] PCT Pub. No.: WO91/16102
PCT Pub. Date: Oct. 31, 1991

[30] Foreign Application Priority Data
Apr. 24, 1990 [DE] Germany ............... 4013048
[51] Int. Cl.⁶ ............................................. A61N 1/36
[52] U.S. Cl. ..................................................... 607/28
[58] Field of Search ............... 128/419 PG; 607/11, 607/27, 28, 13, 64, 12

[56] References Cited
U.S. PATENT DOCUMENTS

| | | | |
|---|---|---|---|
| 3,713,449 | 1/1973 | Mulier | 607/11 |
| 3,757,792 | 9/1973 | Mulier et al. | |
| 3,759,265 | 9/1973 | Thaler et al. | |
| 4,290,430 | 9/1981 | Bihn et al. | |
| 4,321,928 | 3/1982 | Elmgvist | |
| 4,402,332 | 9/1983 | Duggan | |
| 4,674,508 | 6/1987 | DeCote | 607/28 |
| 4,729,376 | 3/1988 | DeCote, Jr. | 607/28 |
| 4,870,974 | 10/1989 | Wang | 607/27 |
| 4,878,497 | 11/1989 | Callaghan et al. | |
| 4,895,152 | 1/1990 | Callaghan et al. | 607/28 |
| 4,979,507 | 12/1990 | Heinz et al. | 607/30 |
| 5,154,172 | 10/1992 | Terry, Jr. et al. | 607/64 |
| 5,165,404 | 11/1992 | Andersson et al. | 607/13 |

FOREIGN PATENT DOCUMENTS 0334675 9/1989 European Pat. Off. .
2342030 3/1975 Germany .

Primary Examiner—Lee S. Cohen
Assistant Examiner—Marianne Parker
Attorney, Agent, or Firm—Hill, Steadman & Simpson

[57] ABSTRACT

In a device for tissue stimulation, the stimulation energy is matched to the stimulation sensitivity of the tissue by altering the stimulation energy in steps upwardly until a tissue reaction is detected, or in steps downwardly until a tissue reaction fails to occur. In order to obtain a safety factor which is expressible in volts with the lowest possible current consumption, stimulation pulses are generated in the determination of the stimulation sensitivity having an amplitude at a voltage which is below the available voltage of a voltage source by a voltage value which corresponds to the safety factor, and the pulse duration is altered in the aforementioned steps. Stimulation subsequently takes place using the pulse duration found in this manner and at a pulse amplitude corresponding to the available voltage.

7 Claims, 3 Drawing Sheets

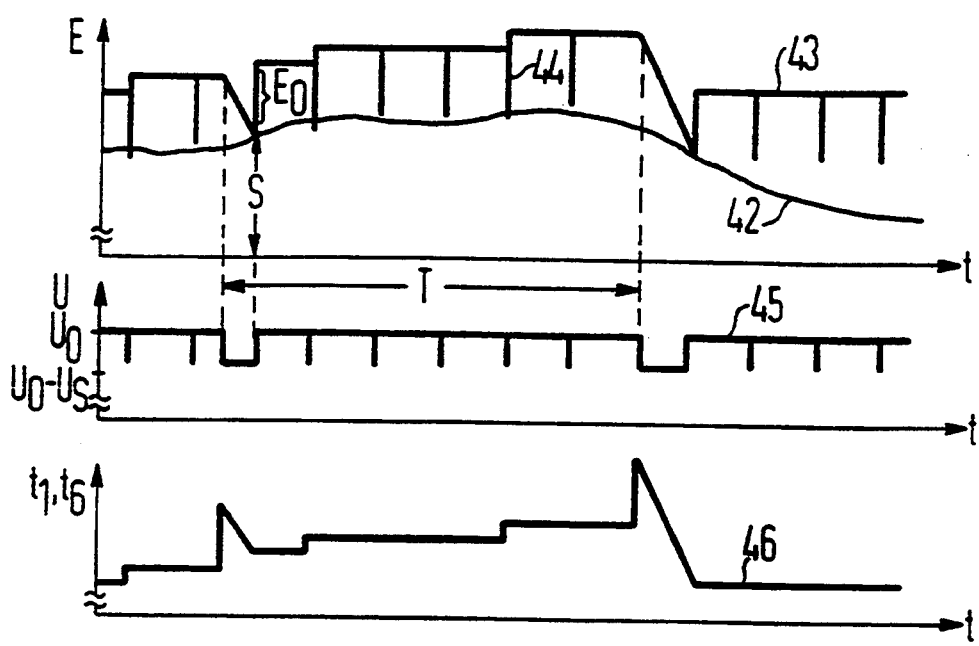
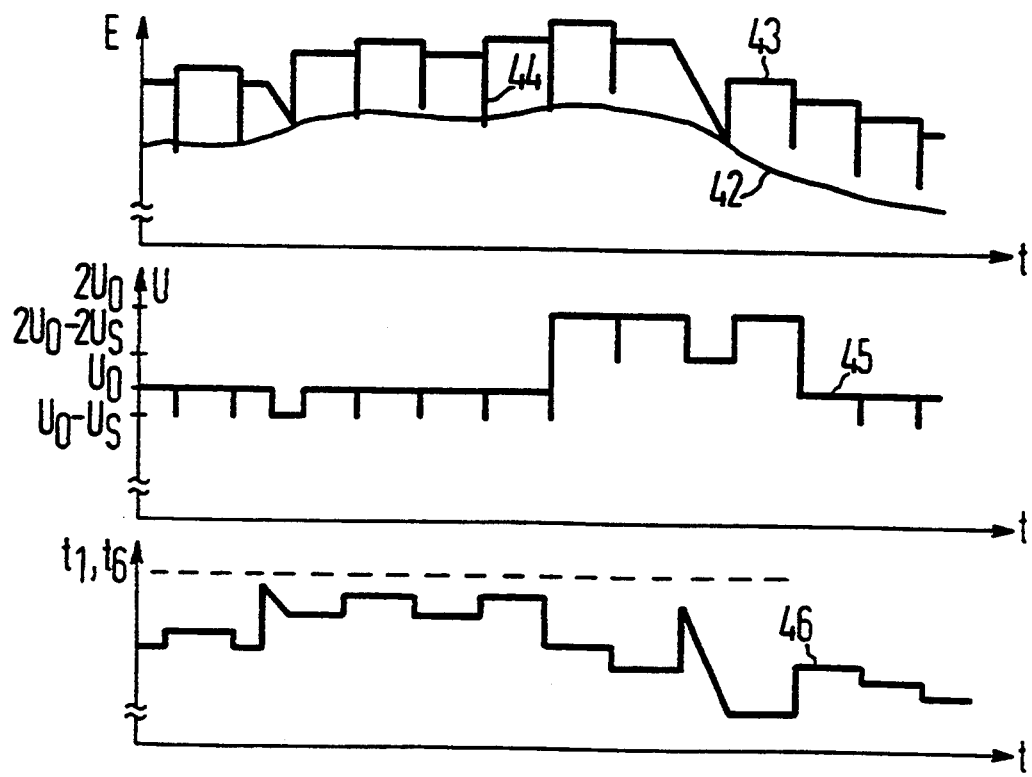

DEVICE FOR TISSUE STIMULATION

BACKGROUND OF THE INVENTION

1. Field of the Invention

The invention relates to a device for tissue stimulation in a living organism, of the type having a stimulation pulse generator, fed from a voltage source, for the generation of stimulation pulses, a detector device to detect the reaction of the tissue to the stimulation and a control device which controls the stimulation pulse generator and which, to determine the stimulation sensitivity of the tissue, causes an alteration of the energy of successively generated stimulation pulses until such time as the detector device detects a change from an absence of the reaction to a reaction or vice versa, the stimulation pulses subsequently being generated with an energy which corresponds to the value determined for the stimulation sensitivity plus a safety factor.

2. Description of the Prior Art

A device of the type is known from U.S. Pat. No. 4,878,497 in the form of a heart pacemaker by which the heart of a patient is excited with the aid of stimulation pulses. In this case, a contraction takes place as reaction of the heart only in circumstances in which the energy of the stimulation pulses exceeds a specified stimulation threshold which is evident from the stimulation sensitivity of the tissue of the heart. In order to keep the energy consumption at a low level when using the known heart pacemaker, the stimulation energy is matched to the alterable stimulation sensitivity by determining the stimulation sensitivity of the tissue of the heart at specified time intervals and subsequently setting the stimulation energy to a value which corresponds to the energy value (stimulation threshold) determined for the stimulation sensitivity plus a safety factor. In order to determine the stimulation sensitivity, the energy of the stimulation pulses is increased successively in steps, proceeding from a value which is below the stimulation threshold, until such time as a reaction of the tissue of the heart to the stimulation is detected by the detector device. After the determination of the stimulation sensitivity and the setting, matched thereto, of the stimulation energy, a regular check is made, until the next procedure of determination by detection of the heart reaction, as to whether the set stimulation energy exceeds the stimulation threshold of the tissue of the heart. If this is not the case, the stimulation energy is increased. In this case and in the determination of the stimulation sensitivity, the alteration of the energy of the stimulation pulses takes place, proceeding from an instantaneous pulse duration, by first increasing the pulse amplitude (electrical current strength) in steps to a specified value, and subsequently the pulse duration is increased in steps and finally, on reaching a maximum pulse duration, the pulse amplitude is increased to a maximum value.

German AS 2,254,928 discloses a heart pacemaker in which, in order to determine the stimulation sensitivity of the tissue of the heart, the pulse amplitude of successive stimulation pulses is reduced in steps, proceeding from a value which is above the stimulation threshold of the tissue of the heart, until such time as an absence of the reaction of the heart is detected.

As is known, among the stimulation pulses which, in the case of a specified stimulation sensitivity of a tissue to be stimulated, are still just capable of triggering a stimulation, those stimulation pulses which have a shorter pulse duration and a greater pulse amplitude exhibit a lower current consumption than stimulation pulses which have a smaller pulse amplitude and a longer pulse duration. Since, especially in the case of implanted devices, the stimulation energy is as a rule drawn from a battery as voltage source, the aim is to achieve the lowest possible drain of charge from the voltage source in conjunction with the generation of the stimulation pulses. The desire also exists, especially on the part of physicians, to be able to express the safety factor between the stimulation threshold of the tissue and the stimulation energy set as a function thereof in the form of an electric voltage, i.e. in volts.

SUMMARY OF THE INVENTION

In a tissue stimulation device according to the invention, of the aforementioned type, in a mode for the determination of the stimulation sensitivity the stimulation pulses are generated with a pulse amplitude, at a voltage below the maximum available voltage of the voltage source by a voltage value corresponding to the safety factor, with the pulse duration of the stimulation pulses being altered in order to alter the stimulation energy, and in a therapy mode, following the determination of the stimulation sensitivity, the stimulation pulses are generated with a pulse amplitude corresponding to the available voltage of the voltage source and the pulse duration is set upon detection of the change in the reaction of the tissue. As a result of the fact that in the period between two successive procedures for the determination of the stimulation sensitivity, stimulation pulses having a pulse amplitude corresponding to the available voltage of the voltage source are generated, the drain of current or charge from the voltage source is as low as possible. In this case, the pulse amplitude is preferably above the last-determined stimulation threshold of the tissue to be stimulated by the safety factor expressed as an electric voltage, i.e. in volts, so that reliable information on the safety factor is supplied by this means to the attending physician.

A situation may arise in which, in the time interval between two successive determinations of the stimulation sensitivity, the stimulation threshold of the tissue to be stimulated increases due to a reduction in the stimulation sensitivity to a level above the set value for the stimulation energy, to prevent this situation in an further embodiment of the it is provided that invention it is provided that after the determination of the stimulation sensitivity until the next determination at recurrent predetermined time intervals, individual stimulation pulses are generated with a pulse amplitude reduced by the safety factor, and the reaction of the tissue is detected by means of the detector device. In the absence of the reaction, for a next stimulation pulses the pulse duration is increased and the pulse amplitude is returned to the value corresponding to the available voltage. In this manner, even in the event of an unpredictably rapid decrease in the stimulation sensitivity, a reliable stimulation is in all cases achieved without unsuccessful attempts at stimulation.

In the simplest case, upon detection of a reaction of the tissue to the respective individual stimulation pulse, the pulse amplitude for the next stimulation pulses may be returned to the value corresponding to the available voltage, with an unaltered pulse duration. In order to achieve an energy-saving matching of the stimulation energy to the stimulation sensitivity even during the period between two determinations of the stimulation sensitivity, preferably upon detection of a reaction of the tissue to a stimulation pulse, the pulse duration for the next stimulation pulses is reduced and the pulse amplitude is returned to the value corresponding to the available voltage.

If a common stimulation electrode is employed for the stimulation and the detection of the stimulation response (reaction) of the tissue, the stimulation response has polarisation phenomena caused by the stimulation in the superimposed thereon tissue, for a period of time until such phenomena become undetectable. In this connection, German-OS 2,342,030 discloses the generation of bipolar stimulation pulses consisting of a first partial pulse, which triggers the stimulation, directly followed by a second partial pulse, of opposite polarity, the energy content of the second partial pulse is dimensioned so that the polarisation phenomena generated by the first partial pulse in the tissue are degraded so rapidly that subsequently a disturbance-free detection of the stimulation response is possible. The energy consumption of biphase stimulation pulses is, however, approximately twice as great as the energy consumption of monophase stimulation pulses with the same effect for the triggering of a stimulation. In order thus to keep the energy consumption at the lowest possible level, according to a further development of the invention in which the stimulation pulse generator and the detector device are connected to a common stimulation electrode, the stimulation pulses to be generated in conjunction with a subsequent detection of the reaction of the tissue are generated in the form of biphase stimulation pulses, and all remaining stimulation pulses are generated in the form of monophase pulses.

In this case, each biphase stimulation pulse preferably consists of partial pulses of differing polarity with a pulse interval between the partial pulses, the partial pulses exhibiting in each instance a substantially equal pulse amplitude and pulse duration. The pulse interval between the partial pulses does indeed prevent a situation in which the effectiveness of the first partial pulse with regard to the triggering of a stimulation is reduced by the following partial pulse. It has been established that the tissue to be stimulated reacts to the biphase stimulation pulses generated by the device according to the invention approximately with the same stimulation sensitivity, and with larger pulse intervals even with increased stimulation sensitivity (i.e. a lower stimulation threshold), as compared with its reaction to monophase stimulation pulses corresponding to the first partial pulse in each case.

As was mentioned in the introduction, the current consumption is lower in the case of stimulation pulses having a shorter pulse duration and a greater pulse amplitude than in the case of stimulation pulses having a low pulse amplitude and a longer pulse duration. However, especially in the case of a detection of the reaction of the tissue to the stimulation, it is necessary to limit the pulse duration to a maximum value, in order to permit any detection at all. Therefore, in a further embodiment of the invention, the energy of the stimulation pulses is altered by altering their pulse duration; proceeding from the pulse amplitude predetermined by the available voltage of the voltage source, between a minimum value and a maximum value. Upon reaching the maximum value, in order to set an even higher energy, the pulse amplitude is set to a value increased by multiplication of the voltage of the voltage source.

DESCRIPTION OF THE DRAWINGS

FIGS. 3 and 4 show respectively, examples of the time progression of the stimulation sensitivity of tissue to be stimulated and the progression of the stimulation energy matched thereto, in the device of FIG. 1.

DESCRIPTION OF THE PREFERRED EMBODIMENT

Figure 1:
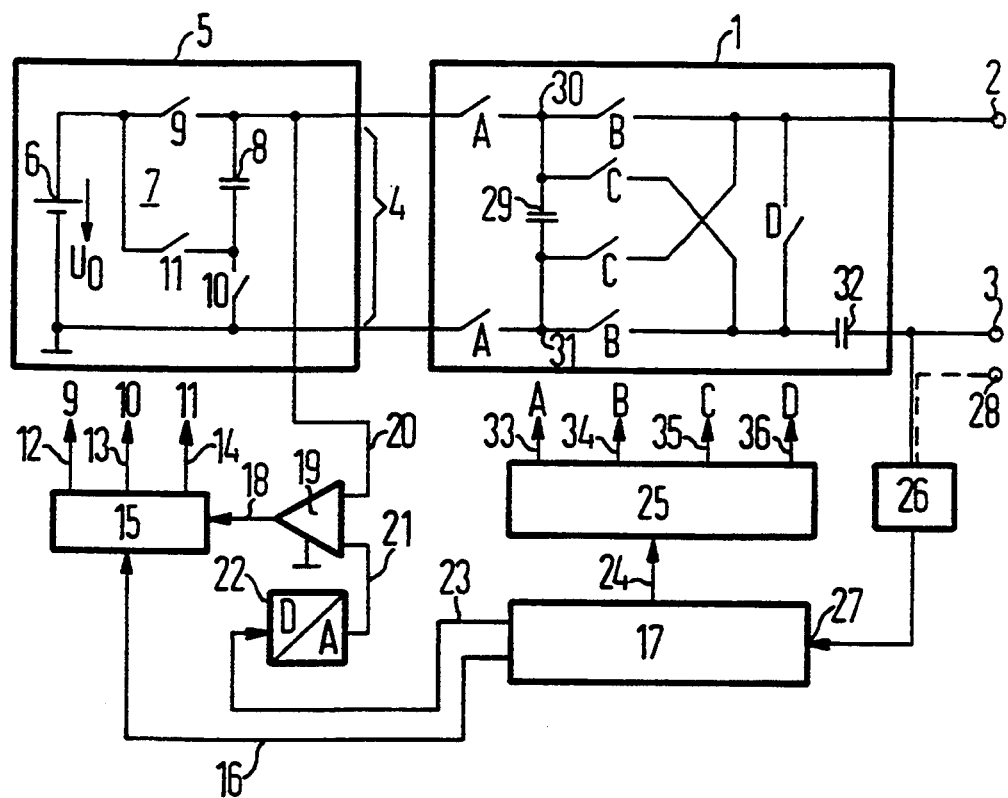
FIG. 1 is a block circuit diagram of an illustrative embodiment of the device according to the invention.

FIG. 1 shows, in an illustrative embodiment of a device according to the invention, a block circuit diagram of a heart pacemaker for tissue stimulation, in this case the stimulation of a heart. The heart pacemaker includes a stimulation pulse generator (1), to which a neutral electrode (2) and a stimulation electrode (3) are connected on the output side. The neutral electrode (2) is formed by the housing (not shown) of the heart pacemaker, while the stimulation electrode (3) is placed in the heart. The stimulation pulse generator (1) is connected, on the input side, to the output (4) of a stimulation voltage generator (5) which supplies the stimulation pulse generator (1) with a predeterminable voltage for the stimulation pulses to be generated.

The stimulation pulse generator (5) contains a battery (6) with a battery voltage $U_0$ and a voltage doubler connection (7), which consists of a capacitor (8) and three individually controllable switches (9, 10, 11). The battery (6) is switchable, by means of the switch designated by (9), directly to the output (4) of the stimulation voltage generator (5). The capacitor (8) is connectable, via the same switch (9) and the switch (10), in parallel to the battery (6), or, when the switches (9, 10) are open and the switch (11) is closed, is connected in a series circuit to the battery (6) at the output (4) of the stimulation voltage generator (5). The switches (9, 10, 11) are individually controlled via respective control lines (12, 13, 14), of a switching pulse generator (15), which is connected to a first output-side control line (16) of a control device (17). The switching pulse generator (15) is connected via an additional control line (18) to the output of a comparator (19), which is connected via a first input (20) to the output (4) of the stimulation voltage generator (5) and via a second input (21) to the output of a digital/analog converter (22). The digital/analog converter (22) is connected on the input side to a second output-side control line (23) of the control device (17). The control device (17) predetermines the value for the voltage to be generated by the stimulation voltage generator (5) and, through the switching pulse generator (15), causes a corresponding control of the switches (9, 10, 11), as is further explained.

The control device (17) is further connected via a third output-side control line (24) to a clock device (25) which, as is further explained below, controls the time progression of the generation of the stimulation pulses in the stimulation pulse generator (1). A detector device (26) is connected the stimulation electrode (3). The detector detector device (26), after emission of a stimulation pulse by the stimulation pulse generator (1), detects the reaction of the tissue and is connected on the output side to a control input (27) of the control device (17). Instead of being connected to the stimulation electrode (3), the detector device (26) may be connected to a measurement electrode (28) disposed in the vicinity thereof, as is shown in broken lines in FIG. 1.

Within the stimulation pulse generator (1), a storage capacitor (29) is connected at its connections (30, 31) via a first pair of switches A to the output (4) of the stimulation voltage generator (5). The storage capacitor (29) is further connected via a second pair of switches B and a third pair of switches C, which are disposed in a bridge circuit, to the neutral electrode (2) and via an output capacitor (32) to the stimulation electrode (3). Depending upon whether the pair of switches B or the pair of switches C is closed, the storage capacitor (29) is connected at its connection designated by (30) to the neutral electrode (2) and at its connection (31) to the output capacitor (32) or conversely, by its connection (31) to the neutral electrode (2) and by the connection (30) to the output capacitor (32). Finally, a switch D is provided which connects the stimulation electrode (3) via the output capacitor (32) to the neutral electrode (2). The pairs of switches A, B and C and the switch D are driven individually, via control lines (33, 34, 35, 36) associated with them, from the clock device (25), as is explained below with reference to FIG. 2.

Figure 2:
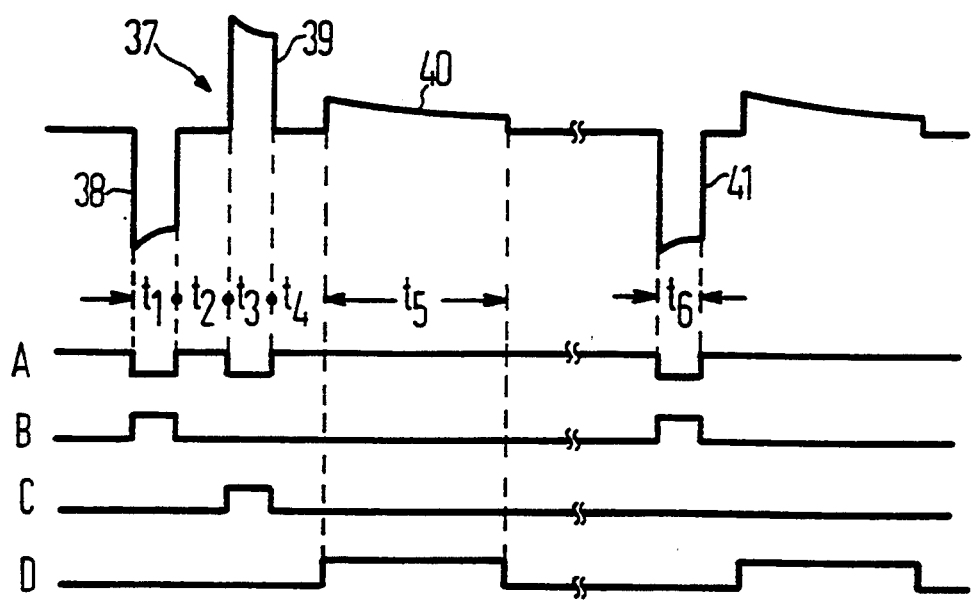
FIG. 2 shows on a time graph, a biphase and a monophase stimulation pulse, as well as control signals required for their generation, for use in the device of FIG. 1.

FIG. 2 shows, on a time graph, an example of a biphase stimulation pulse (37), which consists of a negative partial pulse (38) followed by a positive partial pulse (39) and a rapid discharge pulse (40) for the output capacitor (32). Also shown are a monophase stimulation pulse (41) and the control signals which are emitted for the generation of the stimulation pulses (37, 41) from the clock device (25) to the pairs of switches A, B and C as well as the switch D, and which are designated correspondingly. A non-zero signal state signifies that the associated switch is closed.

As long as the pair of switches A is closed, the storage capacitor (29) is charged to the output voltage which is predetermined by the control device (17) and is generated by the stimulation voltage generator (5). In this case, the storage capacitor (29) is charged to the voltage $U_0$ of the battery (6), in that, when the switches (10, 11) are open, the switch (9) is closed. In order, on the other hand, to charge the storage capacitor (29) to a value between the voltage $U_0$ and the double battery voltage (2) $U_0$, the desired value is fed from the control device (17) in the form of a digital value via the second output-side control line (23) to the digital/analog converter (22), which applies the corresponding analog voltage value to the second input (21) of the comparator (19). At the same time, the switches (9, 10) and the switch (11) are alternatingly closed and opened with a high frequency of succession, so that electric charge is pumped in charge packets from the battery (6) into the storage capacitor (29). As soon as the voltage at the output (4) of the stimulation voltage generator (5), and thus at the first input (20) of the comparator (19), reaches the value of the reference voltage at the second input (21) of the comparator (19), the latter switches the switches (9, 11) into an open condition via the control line (18) and interrupts the operation of the charge pump. The principle of the voltage increase is also known from European Application 0,026,481, which also shows further possibilities for the voltage increase which are applicable in conjunction with the device according to the invention.

In order to generate the biphase stimulation pulse (37) between the stimulation electrode (3) and the neutral electrode (2), when the pair of switches A is open the pair of switches B is closed for a period of time $t_1$ and after a subsequent interval $t_2$ the pair of switches C is closed for a period of time $t_3$; finally, after a further interval $t_4$ the switch D is closed for a period of time $t_5$, whereby the output capacitor (32) is rapidly discharged. The pulse durations $t_1$ and $t_3$ and the pulse amplitudes of the partial pulses (38, 39) are in each instance substantially equal; in this case, the pulse durations $t_1$ and $t_3$ are preferably varied within the range between 0.03 ms and 1 ms. The pulse interval $t_2$ between the two partial pulses (38, 39) has a duration of approximately 1 ms and the duration of the rapid discharge pulse (40), which may directly adjoin the positive partial pulse (39), even without an interval $t_4$ amounts to approximately 4 ms. The indicated values are only guideline values and are variable; in this case, however, the entire biphase stimulated pulse (37) is preferably ended at the latest after 6 to 7 ms, and the reaction of the stimulated tissue is detected by the detector device (26) connected to the stimulation electrode (3). At this point in time, the polarisation, generated in the tissue by the stimulating negative partial pulse (38), has fallen, even in the case of a relatively high stimulation energy, to a few mV, so that an unambiguous detection, substantially free from superimpositions due to the polarisation phenomena, of the reaction of the tissue is permitted. As a result of the pulse interval $t_2$ between the two partial pulses (38, 39), the situation is prevented in which the stimulation-triggering effect of the first partial pulse (38) is reduced by the following partial pulse (39), in which procedure, with increasing pulse interval $t_2$, it was even possible to detect a slight increase in the stimulation-triggering effect.

If the reaction of the stimulated tissue is detected via the measurement electrode (28) which is adjacent to the stimulation electrode (3), then in place of the biphase stimulation pulse (37) it is possible to use the monophase stimulation pulse (41) for the tissue stimulation, which monophase stimulation pulse exhibits only one half of the current consumption. This is due to the fact that the potential of action in the tissue passes to the measurement electrode (28) with a time delay coming from the stimulation electrode (3), so that in this time the polarisation phenomena have been substantially reduced.

The monophase stimulation pulse designated by (41) is generated by closure of the pair of switches B; subsequently, the output capacitor (32) is discharged by closure of the switch D by a rapid charge pulse. As shown by FIG. 2, the energy content of the monophase stimulation pulse (41) at equal pulse amplitude and pulse duration $t_6 = t_1 = t_3$, is lower by one half than that of the biphase stimulation pulse (37). However, in spite of their differing energy content, both stimulation pulses (37, 41) show approximately the same stimulation-triggering effect in tissue stimulation. Accordingly, the biphase stimulation pulses (37) are generated only in circumstances in which the reaction of the tissue to the stimulation is to be picked up via the stimulation electrode (3); otherwise, monophase stimulation pulses in accordance with the pulse (41) are generated for the tissue stimulation. This is explained with reference to FIGS. 3 and 4.

In FIGS. 3 and 4, in each instance in the upper time graph, a possible progression, designated by (42), of the stimulation sensitivity of the tissue to be stimulated is plotted as a function of the time t. The stimulation sensitivity is expressed by an energy value E (or an electric voltage or a current), which a stimulation pulse must at least exhibit for a successful stimulation of the tissue. In order to guarantee a successful stimulation at all times, the tissue could be constantly stimulated with a maximum energy. However, in this case the energy requirement would be very high. Accordingly, the stimulation energy is matched to the variable stimulation sensitivity (42) of the tissue in accordance with the progression of the curve designated by (43). To this end, at periodic time intervals T the current stimulation sensitivity of the tissue is determined, with the tissue being stimulated by biphase stimulation pulses in the event of the connection of the detector device (26) to the stimulation electrode (3) and otherwise by monophase stimulation pulses (37, 41, cf. FIG. 2). At the same time the reaction of the tissue to the stimulation is detected by the detector device (26). As long as, on each occasion, a reaction of the tissue is detected, the stimulation energy of the immediately following biphase or monophase stimulation pulse is reduced until such time as a reaction of the tissue is absent, since the current stimulation sensitivity S was not reached. In this case, the stimulation sensitivity S corresponds to the current minimum required stimulation energy, in order to be able to trigger any stimulation at all. After determination of the stimulation sensitivity S, for the further stimulation of the tissue, monophase stimulation pulses (41) are generated, having an energy $E=S+E_0$ which is greater than the above stimulation sensitivity S by a safety factor $E_0$, until, after the time interval T has elapsed, the stimulation sensitivity (42) of the tissue is again determined in the above-described manner. The safety factor $E_0$ can be defined by a fixed value or a percentage of the value S found for the stimulation sensitivity (42). In the case of the curve progression (43), the energy of the stimulation pulses employed is normalised with respect to the component relevant for stimulation purposes (preceding i.e., for the biphase stimulation pulses (37), only the energy of the first stimulation-triggering partial pulse (38) is taken into consideration), so that the actual expenditure of energy in the biphase stimulation is approximately twice as great as in the case of the monophase stimulation. In order to achieve a rapid matching of the stimulation energy (43) to the progression (42) of the stimulation sensitivity, while keeping the accumulation of the relatively energy-intensive detection of the stimulation sensitivity (applicable in the case of the use of biphase stimulation pulses (37)), at the lowest possible level, the time interval T is varied until, in each case, the following determination of the stimulation sensitivity. The time interval T is varied as a function of its alteration between the current and the preceding determination; in this case, as the alteration becomes greater the time interval T is reduced.

Between two successive procedures for the determination of the stimulation sensitivity, an individual biphase stimulation pulse (or in the event of the connection of the detector device (26) to the measurement electrode (28) an individual monophase stimulation pulse (44)), is generated "periodically (such as after every tenth monophase stimulation pulse (41))" with an energy reduced by the safety factor $E_0$, and a check is made by the detector device (26) as to whether the stimulation energy thus reduced continues to be above the stimulation sensitivity (42). If this is not the case, then the stimulation energy for the following monophase stimulation pulses is increased by an amount exceeding the safety factor $E_0$. In contrast to FIG. 3, FIG. 4 shows an illustrative embodiment in which, for the case in which the stimulation energy (43) reduced by the safety factor $E_0$ exceeds the stimulation sensitivity (42), the stimulation energy for the following monophase stimulation pulses is increased to a smaller amount than that of the safety factor $E_0$. For the periodic generation of the individual stimulation pulses (44), the control device (17) shown in FIG. 1 includes a software or hardware counter (not shown in FIG. 1) which counts the monophase stimulation pulses (41) and, on reaching a predetermined count (in this case 10), is reset and causes the emission of the individual stimulation pulse (44).

Each of the lower time graphs in FIGS. 3 and 4 show the manner in which the progression of the stimulation energy (43) of the stimulation pulses is set by altering the pulse amplitude U and pulse duration $t_1$, $t_6$. In this case, the progression, designated by (45) in FIG. 3, of the pulse amplitude shows that the pulse amplitude, with the exception of the times in which a detection of the reaction of the tissue takes place, invariably corresponds to the available battery voltage $U_0$. Only in the times in which the reaction of the tissue to the stimulation is also monitored at the same time as the generation of the stimulation pulses, is the pulse amplitude U reduced by a voltage value $U_s$ corresponding to the safety factor $E_0$. Moreover, the alteration of the stimulation energy (43) takes place by variation of the pulse duration $t_1$ or $t_6$ of the stimulation pulses corresponding to the curve designated by (46). FIG. 4 further shows that in circumstances in which the pulse duration $t_1$, $t_6$ threatens to exceed a maximum value indicated by a broken line, a doubling of the stimulation amplitude U to $2U_0$ takes place. In this case also, stimulation pulses having a reduced pulse amplitude U are generated in conjunction with the detection of the stimulation sensitivity, in which case the reduction preferably amounts to $2U_s$, in order to obtain a constant safety factor $E_0$ which is independent of the pulse amplitude $U_s$. The doubling of the pulse amplitude is also explained with reference to FIG. 5. Thus, FIGS. 3 and 4 show that in the determination of the stimulation sensitivity (42), the stimulation pulses are generated with a pulse amplitude, the voltage U of which is below the maximum available voltage $U_0$ of the voltage source (6) by a voltage value $U_s$ corresponding to the safety factor $E_0$, in which case to alter the stimulation energy (43) the pulse duration $t_1$, $t_6$ of the stimulation pulses is altered. Following the determination of the stimulation sensitivity S, the stimulation pulses are generated with a pulse amplitude corresponding to the available voltage $U_0$ of the voltage source (6). Thus, outside the times in which the stimulation sensitivity of the tissue is detected, the pulse amplitude is advantageously above the last-determined stimulation threshold S of the tissue to be stimulated, by the safety factor $U_s$ expressed as an electrical voltage, i.e. in volts, so that this provides the physician in charge with reliable information on the safety factor $E_0$ or $U_s$. As a result of the fact that in the period T between two respective procedures for the determination of the stimulation sensitivity the stimulation pulses are generated with a pulse amplitude corresponding to the available voltage $U_0$ of the voltage source (6), as is explained below with reference to FIG. 5, the drain of current or charge from the voltage source (6) is as low as possible.

Figure 5:
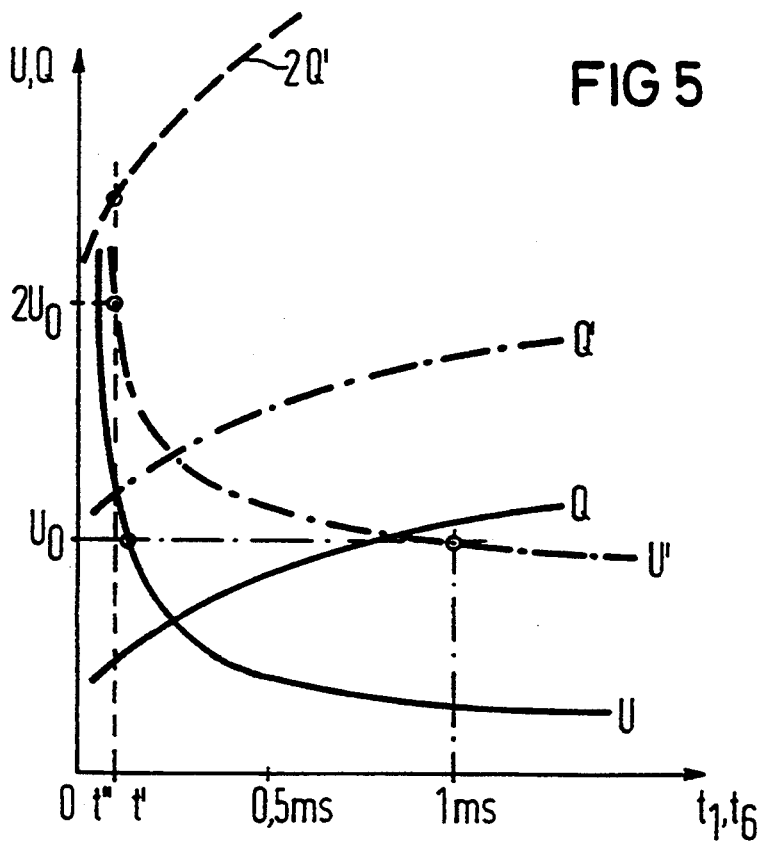
FIG. 5 shows, on a graph, the minimum voltage and charge, required for tissue stimulation in the case of a specified stimulation sensitivity, of a stimulation pulse as a function of its pulse duration in the device of FIG. 1.

FIG. 5 shows, on a graph for a specified stimulation sensitivity of the tissue, the minimum voltage (pulse amplitude) U and charge Q, required for the stimulation of a stimulation pulse as a function of its pulse duration, which, in the case of the biphase stimulation pulse (37, cf. FIG. 2), is the pulse duration $t_1$ of the first stimulating partial pulse (38) and, in the case of the monophase stimulation pulse (41), is the pulse duration $t_6$ thereof. In the case of the biphase stimulation pulse (37), on account of the second partial pulse (39), the charge is in total twice as great, so that the curve progression Q, in comparison with the monophase pulse (41), reproduces only one half of the total charge of the biphase stimulation pulse (37).

As can be recognised, the values for the voltage U increase as the pulse duration $t_1$, $t_6$ decreases, while at the same time the charge Q, which corresponds to the product of the current strength and the pulse duration $t_1$, $t_6$ of the stimulation pulse, decreases. With decreasing stimulation sensitivity of the tissue, the curves Q and U are displaced upwards, as is indicated by the curved paths Q' and U'. If, as in the case of the battery (6, cf. FIG. 1), a specified voltage $U_0$, e.g. 2.5 V, is available, then in the case of the stimulation sensitivity defined by the curve progressions Q and U, the functional progression of the charge Q is decisive for the purposes of the determination of the withdrawal of charge from the battery (6), i.e. of the current consumption. As shown by FIG. 5, the current consumption (i.e. the withdrawal of charge) is then minimum in circumstances in which the entire available voltage $U_0$ is utilized for the generation of the stimulation pulse; in this case, the result is a pulse duration t'. If the stimulation sensitivity of the tissue decreases, as is illustrated by the voltage curve U' and the associated charge curve Q', then an increase in the stimulation energy is required for the successful stimulation. To this end, with constant stimulation voltage $U_0$, the pulse duration $t_1$, $t_6$ of the stimulation pulses is increased until such time as a value of approximately 1 ms is reached. Beyond this value, the total duration in the case of the bipolar stimulation pulse (37) would become too long for a detection of the reaction of the tissue to the stimulation, for which reason in order to achieve a further increase in the stimulation energy a doubled battery voltage $2U_0$ is set by means of the voltage doubler circuit (7, cf. FIG. 1), whereby a reduction of the pulse duration $t_1$ to $t_2'$ arises. However, the voltage doubling also involves a doubling of the battery current, i.e. of the withdrawal of charge from the battery (6); this is illustrated by the charge curve 2Q'. As shown by FIG. 5, this doubling of the withdrawal of charge from the battery (6) is only partially reduced in that in the case of the pulse amplitude increased to $2U_0$ a smaller pulse duration $t_2'$ is required for the stimulation. Thus, to reduce the withdrawal of charge from the battery (6) the voltage doubling is activated only when, in the case of the stimulation with the available battery voltage $U_0$, the pulse duration $t_1$, $t_6$ exceeds a predetermined maximum value (in this case, 1 ms).

Although modifications and changes may be suggested by those skilled in the art, it is the intention of the inventors to embody within the patent warranted hereon all changes and modifications as reasonably and properly come within the scope of their contribution to the art.

I claim:

1. A device for tissue stimulation in a living organism comprising:
   a voltage source;
   means, fed from said voltage source having a maximum available voltage, for generating stimulation pulses at a stimulation energy;
   means adapted for interacting with tissue for delivering said stimulation pulses to said tissue;
   means adapted for interacting with tissue to which said stimulation pulses have been delivered for detecting a reaction of said tissue following a stimulation pulse, said tissue exhibiting a stimulation sensitivity;
   control means for operating said means for generating stimulation pulses, during a mode for determining the stimulation sensitivity of said tissue, for causing said means for generating stimulation pulses to alter said stimulation energy from pulse-to-pulse in steps by generating stimulation pulses each having a pulse amplitude at a voltage below said maximum available voltage by a selected safety factor and respectively having a pulse duration altered in steps starting from a first duration until a change in the reaction of said tissue to one of said stimulation pulses is detected by said means for detecting, and for operating said means for generating stimulation pulses, during a therapy mode, for causing said means for generating stimulation pulses to emit stimulation pulses each having a pulse amplitude at said maximum available voltage and each having a pulse duration equal to the pulse duration of said one of said stimulation pulses.

2. A device as claimed in claim 1 wherein said means for detecting includes means for periodically re-detecting said reaction of said tissue at predetermined time intervals and wherein said control means includes means, operable in said mode for determining the stimulation sensitivity and responsive to an absence of a reaction to said one of said stimulation pulses, for increasing the pulse duration of subsequent stimulation pulses, following said absence, in steps and setting a pulse amplitude for said subsequent stimulation pulses at said maximum available voltage.

3. A device as claimed in claim 2 wherein said control means includes means, operable during said mode for determining said stimulation sensitivity and responsive to the detection of a reaction of said tissue to one of said subsequent stimulation pulses, for returning the pulse amplitude of all stimulation pulses, following the detection of a reaction, to said maximum available voltage with said first pulse duration.

4. A device as claimed in claim 2 wherein said control means includes means, operable during said mode for determining the stimulation sensitivity and responsive to the detection of a reaction of said tissue to said one of said subsequent stimulation pulses, for reducing the pulse duration of stimulation pulses, following the detection of a reaction, in steps and maintaining the pulse amplitude of said following stimulation pulses at said maximum available voltage.

5. A device as claimed in claim 1 further comprising a common stimulation electrode connected to said means for generating stimulation pulses and to said means for detecting the reaction of said tissue, and wherein said control means, during said mode for determining said stimulation sensitivity of said tissue, causes said means for generating stimulation pulses to generate biphase stimulation pulses, and during said therapy mode, causes said means for generating stimulation pulses to generate monophase stimulation pulses.

6. A device as claimed in claim 5 wherein said control means causes said means for generating stimulation pulses to generate biphase stimulation pulses consisting of partial pulses of differing polarity with a pulse interval between said partial pulses, and wherein said partial pulses in each biphase stimulation pulse have a substantially equal pulse amplitude and a substantially equal pulse duration.

7. A device as claimed in claim 1 wherein said control means includes means, operable during said mode for determining the stimulation sensitivity of said tissue, for causing said means for generating stimulation pulses to alter said pulse duration of said stimulation pulses between a maximum value and a minimum value and, upon reaching said maximum value of said pulse duration, to set said pulse amplitude at a value obtained by multiplication of said maximum available voltage by a factor greater than 1.

* * * * *